United States Patent [19]
Zuech

[11] 3,956,177
[45] May 11, 1976

[54] RHODIUM HYDROFORMYLATION CATALYST

[75] Inventor: Ernest A. Zuech, Bartlesville, Okla.

[73] Assignee: Phillips Petroleum Company, Bartlesville, Okla.

[22] Filed: July 5, 1973

[21] Appl. No.: 376,519

Related U.S. Application Data

[63] Continuation-in-part of Ser. No. 173,689, Aug. 20, 1971, abandoned.

[52] U.S. Cl. ................ 252/428; 252/431 N; 252/431 P; 260/604 HF; 252/429 B
[51] Int. Cl.$^2$ ............... B01J 31/18; B01J 31/22
[58] Field of Search ........ 252/429 B, 431 N, 431 P, 252/428

[56] References Cited
UNITED STATES PATENTS

| | | | |
|---|---|---|---|
| 3,098,843 | 7/1963 | Luttinger | 252/431 P |
| 3,511,885 | 5/1970 | Hughes | 252/431 P |
| 3,558,517 | 1/1971 | Hughes et al. | 252/431 N |
| 3,560,539 | 2/1971 | Booth | 252/431 P |
| 3,660,493 | 5/1972 | Johnson et al. | 252/431 P |

Primary Examiner—Patrick P. Garvin

[57] ABSTRACT

Novel compositions and novel hydroformylation catalysts are prepared by the interaction of an organorhodium halide of the formula $(L)_n Rh(X)_m$, wherein X is chlorine, bromine or iodine, L is a cyclic diene or a cyclic triene, $n$ equals 1 or 2, $m$ equals 1 or 2, the sum of $n + m$ equals 2 or 3; hydrazine or a hydride of Group IA, IIA or IIIA metals; and a phosphorus containing adjuvant of the formula $L'_3 P$, wherein each $L'$ individually represents aryl, aryloxy, alkaryl, aralkyl, alkaryloxy, aralkoxy, alkyl or alkoxy radicals. The hydroformylation catalysts promote the conversion of olefins to linear aldehydes.

32 Claims, No Drawings

RHODIUM HYDROFORMYLATION CATALYST

This application is a continuation-in-part of copending application Ser. No. 173,689, filed Aug. 20, 1971, now abandoned.

This invention relates to organorhodium compositions, methods of preparing organorhodium compositions and to the use of organorhodium compositions as catalysts for hydroformylation reations.

Hydroformylation reactions are frequently carried out at relatively high pressures in order to maintain stable active catalyst systems. Representative active catalyst systems include dicobaltoctacarbonyl and carbonyls of other Group VIII metals including rhodium, ruthenium, iridium, and Group VIII metal carbonyls modified by ligands of organic compounds derived from Group V elements such as trialkyl and triaryl phosphines, arsines and stibines.

It is an object of this invention to prepare hydroformylation catalysts that are active at moderate temperatures and pressures. Another object of this invention is to caralyze hydroformylation reactions at moderate temperatures and pressures.

According to this invention, hydroformylation catalysts are prepared by combining an organorhodium halide, and a metal hydride or hydrazine in the presence of a phosphorus containing adjuvant. Also, according to this invention, hydroformylation reactions are carried out in the presence of a hydroformylation catalyst prepared by combining an organorhodium halide, and a metal hydride or hydrazine in the presence of a phosphorus containing adjuvant.

Suitable organorhodium catalyst compositions are obtained by combining an organorhodium halide and hydrazine or a Periodic Table Group IA, IIA, IIIA metal hydride in the presence of a phosphorus containing adjuvant of the general formula $L'_3P$.

Suitable organorhodium halides include compounds represented by the formula:

wherein X is chlorine, bromine or iodine; L is an unsaturated hydrocarbon group selected from cyclic dienes or cyclic trienes containing from 6 to 16 carbon atoms, $n$ represents an integer of from 1 to 2, $m$ represents an integer of from 1 to 2, and the sum of $n$ plus $m$ is equal to 2 or 3. Representative unsaturated hydrocarbon groups include unsaturated hydrocarbyl radicals or olefins, such as: 1,3-cyclohexadienyl; 1,5-cyclooctadienyl; 1,5-cyclooctadiene; 5-sec-butyl-1,3-cyclohexadienyl; dicyclopentadiene; 3,7-dimethyl-1,5-cyclooctadienyl, and cyclododeca-1,5,9-trienyl.

Any "phosphorus containing adjuvant" represented by the formula $L'_3P$ can be employed, wherein each $L'$ is the same or a different hydrocarbyl or hydrocarbyloxy radical. Illustrative L' radicals include aryl or aryloxy radicals having 6 to 12 carbon atoms; alkaryl, aralkyl, alkaryloxy, or aralkoxy radicals having 7 to 12 carbon atoms; and alkyl or alkoxy radicals having 1 to 12 carbon atoms; and combinations thereof. Representative radicals include phenyl; naphthyl; p-tolyl; 2,5-dimethylphenyl; 4-tert-butylphenyl; 4-isopentylphenyl; benzyl; 4-phenylbutyl; 4-phenylcyclohexyloxy; 2-methylphenoxy; 4-cyclohexylphenoxy; benzyloxy; 2-phenylethoxy; 6-phenylhexyloxy; methyl; ethyl; n-butyl; sec-butyl; tert-octyl; n-dodecyl; phenoxy; methoxy; ethoxy; propyloxy; 4,4-dimethylcyclohexyloxy; alpha-naphthyloxy; and beta-naphthyloxy.

The reducing agent can be hydrazine or any metal hydride selected from metals of the Periodic Table Groups IA, IIA, and IIIA. Representative metal hydrides include lithium hydride (LiH); sodium hydride (NaH); sodium borohydride ($NaBH_4$); cesium hydride (CsH); calcium hydride ($CaH_2$); strontium hydride ($SrH_2$); barium hydride ($BaH_2$); as well as any mixture thereof.

Preparation of the hydroformylation catalyst can be carried out in any suitable manner. For example, the catalyst-forming reactants, i.e., organorhodium halide, metal hydride or hydrazine, and phosphorus containing adjuvant are admixed in any order to form a homogeneous catalyst composite, i.e., an intimate mixture of the catalyst-forming reactants, The catalyst-forming reactants can be admixed at any suitable temperature or pressure providing an intimate mixture is formed at some point in time. Generally, temperatures within the range of from about −80°C to about 100°C are considered to be suitable. The ratio of phosphorus to rhodium contained by the catalyst compositions can vary widely. Catalysts containing mole ratios within the range of from 100:1 to 1:100 moles of phosphorus:rhodium are considered to be suitable. Preferably, at least 1 mole of phosphorus per mole of rhodium is present in the catalyst compositions. Even more preferred are catalyst compositions that contain in excess of 1 mole of phosphorus per mole of rhodium since the ratio of linear-to-branched aldehyde product increases, as the ratio of phosphorus to rhodium increases. Thus the mole ratio of phosphorus to rhodium in the catalyst composition is preferably in the range of about 1:1 to about 50:1 and more preferably is in the range of about 2:1 to about 25:1. The olefin can be charged before, during, or after the reduction of the rhodium complex.

The mole ratio of metal hydride or hydrazine to the rhodium in the total catalyst composition will generally be in the range of about 0.25:1 to about 25:1, preferably in the range of about 1:1 to about 20:1, and more preferably in the range of about 2:1 to about 15:1.

The reactant contact time period for the formation of the catalyst is any suitable time period, providing the time period is sufficient to permit the intimate mixing of the reactants. In general, the contact time can vary from a few seconds to as long as several hours depending on the relative degree of mixing, the temperature, the pressure, the miscibility of the catalyst-forming reactants and/or the resulting catalyst composite. The contact time will usually be in the range of about 30 seconds to about 6 hours, and preferably will be in the range of about 5 minutes to about 60 minutes. The contact temperature will usually be in the range of about 25° to about 125°C, and preferably will be in the range of about 40° to about 100°C. The hydroformylation catalyst composite formed by the admixture of catalyst-forming reactants does not have to be isolated from the reactant mixture and may be used directly in a hydroformylation process without further purification or modification. However, it is generally desirable, particularly with the metal hydrides, to neutralize the unreacted excess reducing agent after the preparation of the catalyst and before the use of the catalyst in the hydroformylation process. This can be accomplished by the addition of a suitable neutralizing agent, for example, a carboxylic acid such as glacial acetic acid or benzoic acid. The preparation of a homogeneous intimate catalyst composite may be carried out by admixing the reactants in the presence of an inert (i.e., not deleterious or reactive in this reaction mixture) diluent or solvent. Representative diluents that may be employed are inert organic diluents, including aliphatic, alicyclic and aromatic hydrocarbons, such as benzene, heptane, cyclohexane, xylene, methylcyclohexane; and ethers such as tetrahydrofuran, dioxane, dibutylether and dimethylether of ethylene glycol; and mixtures thereof. Since ethers exhibit a high degree of solubility for the reactants and catalyst composites, ethers are considered to be the preferred diluents. If a solvent or diluent is employed in the preparation of the catalyst composite, the solvated or diluted catalyst can be added directly to the hydroformylation reaction zone without separation from the catalyst composite, or if desired, the solvent can be removed by any convenient separation procedure, such as distillation or solvent extraction.

Catalyzed hydroformylation reactions can be carried out by contacting an olefin with carbon monoxide and hydrogen in the presence of the catalyst compositions described herein under suitable reaction conditions. Reaction temperatures may vary widely. Generally, temperatures in the range of about 0° to about 100°C are considered to be suitable; however, temperatures in the range of about 50°C to about 75°C are preferably employed since optimum reaction rates and end product selectivity result wherein hydroformylation reactions are conducted within the range of 50° to 75°C. Since pressurized reaction conditions increase the solubility of carbon monoxide and hydrogen in the reaction media, which results in increased reaction rates, pressurized reaction conditions are preferred. Any suitable pressure for the mixture of carbon monoxide and hydrogen can be employed, including pressures within the range of from 0 to 1000 psig. Excellent reaction rates and end product selectivity values are obtained when reactions are carried out at pressures in the range of 50 to 150 psig. The hydroformylation reaction can be conducted for any desired suitable length of time, but the reaction time will generally be in the range of about 5 minutes to about 24 hours and preferably will be in the range of about 1 hour to about 3 hours. Any suitable mole ratio of olefin-to-rhodium can be employed. The rhodium-to-olefin ratio will generally be in the range of about 1:1 to about 1:1,000,000, but rhodium-to-olefin ratios varying from 1:100 to 1:500 are preferred for more efficient utilization of the catalyst, since the reaction rate increases as the ratios of rhodium-to-olefin increase. Any suitable ratio of carbon monoxide to hydrogen can be employed. The carbon monoxide-to-hydrogen mole ratio will generally be in the range of from 100:1 to 1:100, and preferably will be in the range of about 25:1 to about 1:25, and more preferably will be in the range of about 3:1 to aobut 1:3.

Any olefin can be employed in the hydroformylation reactions. Suitable olefins include compounds containing at least one >C=C< group. Representative olefins include compounds of the formula

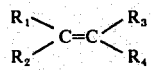

wherein $R_1$, $R_2$, $R_3$ and $R_4$, are the same or different, and represent hydrogen, saturated or unsaturated hydrocarbyl radicals, such as alkyl, alkenyl, cycloalkyl, cycloalkenyl, and aryl radicals or any combinations thereof such as cycloalkaryl, arylcycloalkyl, aralkyl, aralkenyl, alkaryl, and alkenylaryl. Olefins containing from 2 to 20 carbon atoms, including both monoolefins and diolefins are preferably employed. Monoolefins that contain from 2 to 10 carbon atoms are even more preferred reactants because of their commercial importance in the preparation of low molecular weight linear aldehydes.

Illustrative olefins include ethylene; propylene; butene-1; butene-2; 2-methylbutene-1; 2-methylbutene-2; pentene-1; hexene-1; 3-ethylhexene-1; octene-1; 2-propylhexene-1; 2,4,4-trimethylpentene-1; decene-2; 4,4-dimethylnonene-1; dodecene-1; 6-propyldecene-1; tetradecene-5; 4-amyldecene-2; hexadecene-1; 4-methyltridecene-2; octadecene-2; octadecene-1; 6,6-dipropyldodecene-3; eicosene-1; vinylcyclohexane; allycyclohexane; styrene; p-methylstyrene; alpahmethylstyrene; propenylbenzene; p-vinylcumene; betavinylnaphthalene; 1,2-dipehnylethylene; allylbenzene; 6-phenylhexene-1; 1,3-diphenylbutene-1; 3-benzylheptene-3; 1,5-hexadiene; o-vinyl-p-xylene; and divinylbenzene, and mixtures thereof.

EXAMPLE I

An oven dried glass reactor vessel was flushed with nitrogen and charged with 0.09 g (0.25 mmole) π-cyclododeca-1,5,9-trienylrhodium(III) dichloride, 0.1 g (2 mmoles hydride) sodium hydride (50% mineral oil), 25 ml dry tetrahydrofuran, and 3.68 g of a 50% solution of tri-alpha-naphthylphosphite (4.0 mmoles phosphite) in tetrahydrofuran. After pressure checking the reactor, the reaction mixture was heated with stirring to 60°C for 0.5 hour. The reactor was cooled to room temperature, vented and charged with 0.34 g benzoic acid dissolved in 25 ml tetrahydrofuran, and 4.2 g (50 mmoles) 1-hexene. The reactor was pressured to 100 psig with a 1:1 mixture of carbon monoxide/hydrogen, and stirred at 60°C for a period of 2 hours.

Analysis of the reaction mixture by gas chromatography showed the following composition (area percent):

| | |
|---|---|
| n-heptaldehyde | 77.5 |
| branched C₇-aldehydes | 5.6 |
| internal hexenes | 16.9 |

The ratio of linear-to-branched aldehydes in the product mixture was 13.9/1.0.

EXAMPLE II

A glass reactor vessel was dried in an oven and flushed with nitrogen before charging a mixture of 0.09 g (0.25 mmole) π-cyclododeca-1,5,9-trienylrhodium-(III) dichloride, 0.1 g (2 mmoles hydride) sodium hydride (50% mineral oil), 3.68 g of a 50% solution of tri-alpha-naphthylphosphite (4 mmoles phosphite) in tetrahydrofuran and 25 ml anhydrous tetrahydrofuran. The reactor and its contents were heated to 60°–65°C with stirring for a period of 30 minutes. After cooling the reactor to room temperature, it was pressured to 25 psig with carbon monoxide, vented, and charged with 0.5 ml glacial acetic acid, 4.2 g (50 mmoles) 1-hexene, and 5 ml dry tetrahydrofuran. The reactor was then pressured to 35 psig with CO followed by a final pressure adjustment to 105 psig with a 1:1 mixture of carbon monoxide/hydrogen. The mixture was heated to 60°C with stirring for a period of 175 minutes. During the reaction period, the system was repressured as necessary with a 1:1 carbon monoxide/hydrogen mixture to maintain 105 psig in the reactor.

After cooling to room temperature, a gas chromatographic analysis of the reaction mixture showed the following composition (area percent):

| | |
|---|---|
| n-heptaldehyde | 81.1 |
| branched $C_7$-aldehydes | 8.9 |
| internal hexenes | 10.0 |

The ratio of linear-to-branched aldehydes in the product mixture was 9.1/1.0.

EXAMPLE III

A mixture of 0.09 g (0.25 mmole) $\pi$-cyclododeca-1,5,9-trienylrhodium(III) dichloride, 0.5 ml (0.62 g, 2 mmoles) triphenylphosphite, 0.1 g (2.6 mmoles) sodium borohydride, and 25 ml anhydrous tetrahydrofuran was charged to a glass reactor vessel, and the reactor was heated to 65°C for a period of 30 minutes. After cooling the reaction mixture to room temperature, 0.5 ml glacial acetic acid, 4.2 g (50 mmoles) 1-hexene, and 5 ml dry tetrahydrofuran were added to the reactor. The system was then pressured to 100 psig with a 1:1 mixture of CO and $H_2$, and the reactor heated with stirring to 75°C for a period of 78 minutes. During the reaction period, the system was repressured with a 1:1 $CO/H_2$ mixture as necessary to maintain 100 psig in the reactor.

The reaction mixture was cooled to room temperature, and gas chromatographic analysis showed the product composition to be that shown below (area percent):

| | |
|---|---|
| n-heptaldehyde | 75.3 |
| branched $C_7$-aldehyde | 8.6 |
| internal hexenes | 16.2 |

The ratio of linear-to-branched aldehydes in the product mixture was 8.7/1.0.

EXAMPLE IV

To an oven-dried glass reactor vessel was added 0.09 g (0.25 mmole) $\pi$-cyclododeca-1,5,9-trienylrhodium-(III) dichloride, 0.1 g (2 mmoles hydride) sodium hydride (50% mineral oil), 1.0 ml (1.24 g, 4 mmoles) triphenylphosphite, and 25 ml anhydrous tetrahydrofuran. The reactor was pressure checked, and the stirred reaction mixture was heated to 60°–65°C for 30 minutes. After cooling to room temperature, 0.5 ml glacial acetic acid, 4.2 g (50 mmoles) 1-hexene and 5 ml dry tetrahydrofuran were added to the reaction mixture, and the reactor was then pressured to 100 psig with a 1:1 $CO/H_2$ mixture. The stirred reaction mixture was heated to 75°C, and repressured as necessary with a 1:1 $CO/H_2$ mixture to maintain a reactor pressure of 100 psig over a 157 minute period.

Gas chromatographic analysis of the product mixture showed the following composition (area percent):

| | |
|---|---|
| n-heptaldehyde | 75.5 |
| branched $C_7$-aldehydes | 12.1 |
| internal hexenes | 12.4 |

The ratio of linear-to-branched aldehydes in the product mixture was 6.2/1.0.

Examples V, VI, and VII are described below and illustrate that catalyst compositions can be recycled and/or reused in hydroformylation processes.

EXAMPLE V

An oven dried glass reactor vessel was charged with 0.09 g (0.25 mmole) $\pi$-cyclododeca-1,5,9-trienylrhodium(III) dichloride, 0.1 g (2 mmoles hydride) sodium hydride (50% mineral oil), 3.68 g of a 50% solution of trialpha-naphthylphosphite (4.0 mmoles phosphite), and 25 ml anhydrous tetrahydrofuran. The reactor was pressure checked before heating the reaction mixture to 55°–60°c for 30 minutes. After cooling the reaction mixture to room temperature, 0.5 ml glacial acetic acid, 4.2 g (50 mmoles) 1-hexene, and 5 ml anhydrous tetrahydrofuran were added to the reactor. The reactor was pressured to 100 psig with a 1:1 mixture of carbon monoxide/hydrogen, and then heated to 60°C for a period of 160 minutes.

Gas chromatographic analysis of the reaction mixture showed the presence of the following components (area percent):

| | |
|---|---|
| n-heptaldehyde | 82.2 |
| branched $C_7$-aldehydes | 5.2 |
| internal hexenes | 11.6 |
| 1-hexene | 1.0 |

The ratio of linear-to-branched aldehydes was 15.8/1.0. A residue of 2.15 g remained after stripping the reaction mixture in vacuo.

EXAMPLE VI

The residue from Example V was dissolved in 25 ml tetrahydrofuran and charged to a glass reactor vessel containing 4.2 g (50 mmoles) 1-hexene and 5 ml dry tetrahydrofuran. The reactor was pressured to 100 psig with a 1:1 mixture of CO and $H_2$, and heated with stirring to 60°C for a period of 131 minutes.

Analysis of the reaction mixture by gas chromatography revealed the following components (area percent):

| | |
|---|---|
| n-heptaldehyde | 81.5 |
| branched $C_7$-aldehydes | 3.9 |
| internal hexenes | 14.7 |

The ratio of linear-to-branched aldehydes was 20.9/1.0, and stripping of the reaction mixture in vacuo gave a 3.1 g residue.

EXAMPLE VII

The residue from Example VI was dissolved in 25 ml tetrahydrofuran and charged to a glass reactor vessel containing 4.2 g (50 mmoles) 1-hexene and 5 ml anhydrous tetrahydrofuran. The procedure of Examples V and VI was essentially repeated with a reaction period of 89 minutes. Analysis by glpc showed the presence of the following components in the product mixture:

| | |
|---|---|
| n-heptaldehyde | 79.2 |
| branched $C_7$-aldehydes | 4.5 |
| internal hexenes | 16.3 |

The ratio of linear-to-branched aldehydes in the product mixture was 17.6/1.0.

EXAMPLE VIII

An oven-dried glass reactor vessel was flushed with nitrogen and charged with 0.09 g (0.25 mmole) π-cyclododeca-1,5,9-trienylrhodium(III) dichloride, 0.1 g (2 mmoles hydride) sodium hydride (50% mineral oil), 3.68 g of a 50% solution of tri-alpha-naphthylphosphite (4.0 mmoles phosphite) in tetrahydrofuran, and 25 ml anhydrous tetrahydrofuran. After the reactor was pressure checked, the stirred reaction mixture was heated to 60°C for 30 minutes. The reactor was cooled and 0.5 ml glacial acetic acid, 5 ml anhydrous tetrahydrofuran, and 2 g (48 mmoles) propylene were added to the reaction mixture. The reactor was pressured to 100 psig with a 1:1 mixture of carbon monoxide/hydrogen, and the stirred reactants were heated to 60°C over a reaction period of approximately 2 hours. Reactor pressure was maintained at 100 psig by adding incremental amounts of the 1:1 mixture of carbon monoxide/hydrogen.

Analysis by glpc showed that the product mixture had the following composition (area percent):

| | |
|---|---|
| n-butyraldehyde | 90.1 |
| isobutyraldehyde | 9.9 |

The ratio of linear-to-branched aldehydes in the product mixture was 9.1/1.0.

EXAMPLE IX

An oven-dried glass reactor vessel was charged with a mixture of 0.09 g (0.25 mmole) π-cyclododeca-1,5,9-trienylrhodium(III) dichloride, 3.68 g of a 50% solution of tri-alpha-napthylphosphite (4.0 mmoles phosphite) in tetrahydrofuran, 0.1 g (3.0 mmoles) 95% hydrazine, 4.2 g (50 mmoles) 1-hexene, and 25 ml anhydrous tetrahydrofuran. After nitrogen flushing and pressure checking the reaction vessel, the system was pressured to 100 psig with a 1:1 mixture of carbon monoxide/hydrogen, and heated to 60°C with stirring over a period of 76 minutes. A pressure of 100 psig was maintained in the reactor during the run by periodically repressuring the system with a 1:1 mixture of CO and $H_2$.

Gas chromatographic analysis of the reaction mixture showed that the following products were present (area percent):

| | |
|---|---|
| n-heptaldehyde | 73.4 |
| branched $C_7$-aldehydes | 6.1 |
| internal hexenes | 19.1 |
| 1-hexene | 1.4 |

The ratio of linear-to-branched aldehydes in the product mixture was 12.0/1.0.

EXAMPLE X

To an oven-dried glass reactor vessel was added 0.09 g (0.25 mmole) π-cyclododeca-1,5,9trienylrhodium-(III) dichloride, 0.1 g (2 mmoles hydride) sodium hydride (50% mineral oil), and 25 ml anhydrous tetrahydrofuran. The reactor was pressure checked, and the stirred reaction mixture was heated to 60°C for 30 minutes under 10 psig of a 1:1 mixture of CO and $H_2$. After cooling to room temperature, 0.5 ml glacial acetic acid, 4.2 g (50 mmoles) of 1-hexene, and 5 ml dry tetrahydrofuran were added to the reaction mixture, and the reactor was then pressured to 100 psig with a 1:1 $CO/H_2$ mixture. The stirred reaction mixture was heated to 75°C over a 140 minute period and there was essentially no up-take of CO and $H_2$ as evidenced by the pressure readings, i.e., the pressure gradually increased from 100 psig to 120 psig during the 140 minute period with apparently little or no hydroformylation taking place during this period.

The reactor was cooled, vented, and charged with 3.68 g of a 50% solution of tri-alpha-naphthylphosphite (4.0 mmoles phosphite) in tetrahydrofuran. The reactor was repressured to 100 psig with a 1:1 mixture of $CO/H_2$ and heated with stirring to 60°C. During this 88 minute reaction period, the reactor was repressured periodically with a 1:1 carbon monoxide/hydrogen mixture in order to maintain 100 psig in the system. After cooling to room temperature, a gas chromatographic analysis of the reaction mixture showed the following composition (area percent):

| | |
|---|---|
| n-heptaldehyde | 88.5 |
| branched $C_7$-aldehydes | 5.55 |
| internal hexenes | 7.09 |
| hexane | trace |

The ratio of linear-to-branched aldehydes in the product mixture was 16.0/1.0.

This example illustrates that a phosphorus containing adjuvant must be present in order that the catalyst compositions be effective as catalyst of hydroformylation reactions.

SUMMARY OF EXAMPLES I – X

| Example No. | Rhodium Halide | Added Adjuvant | Molar Ratio Phosphorus/ Rhodium | Ratio of Linear/Branched Aldehyde Products | Reducing Agent | Olefin Feedstock |
|---|---|---|---|---|---|---|
| I | $(C_{12}H_{17})RhCl_2$ | $(C_{10}H_7O)_3P$ | 16/1.0 | 13.9/1.0 | Sodium hydride | 1-Hexene |
| II | $(C_{12}H_{17})RhCl_2$ | $(C_{10}H_7O)_3P$ | 16/1.0 | 9.1/1.0 | Sodium hydride | 1-Hexene |
| III | $(C_{12}H_{17})RhCl_2$ | $(C_6H_5O)_3P$ | 8/1.0 | 8.7/1.0 | Sodium borohydride | 1-Hexene |
| IV | $(C_{12}H_{17})RhCl_2$ | $(C_6H_5O)_3P$ | 16/1.0 | 6.2/1.0 | Sodium hydride | 1-Hexene |
| V | $(C_{12}H_{17})RhCl_2$ | $(C_{10}H_7O)_3P$ | 16/1.0 | 15.8/1.0 | Sodium hydride | 1-Hexene |
| VI | $(C_{12}H_{17})RhCl_2$ | $(C_{10}H_7O)_3P$ | 16/1.0 Catalyst recycled | 20.9/1.0 | (Catalyst Recycle) | 1-Hexene |
| VII | $(C_{12}H_{17})RhCl_2$ | $(C_{10}H_7O)_3P$ | 16/1.0 Catalyst recycled | 17.6/1.0 | (Catalyst Recycle) | 1-Hexene |
| VIII | $(C_{12}H_{17})RhCl_2$ | $(C_{10}H_7O)_3P$ | 16/1.0 | 9.1/1.0 | Sodium hydride | Propylene |
| IX | $(C_{12}H_{17})RhCl_2$ | $(C_{10}H_7O)_3P$ | 16/1.0 | 12.0/1.0 | Hydrazine | 1-Hexene |
| X | $(C_{12}H_{17})RhCl_2$ | $(C_{10}H_7O)_3P$ | 16/1.0 | 16.0/1.0 | Sodium hydride | 1-Hexene |

The foregoing summary illustrates that the structure of the phosphorus containing adjuvant affects the ratio of linear aldehyde/branched aldeyde product obtained under hydroformylation reaction conditions. For example, the tri-alpha-naphthylphosphite system gave a higher ratio of linear aldehyde/branched aldehyde than did the triphenylphosphite system (see Examples IV and V). Examples V, VI, and VII demonstrate that the catalyst of the present invention can be effectively recycled. Examples I, III, and IX illustrate the use of various reducing agents such as sodum hydride, sodium borohydrde and hydrazine. Examples III and IV show the use of triphenylphosphite adjuvant in the hydroformylation of 1-hexane whereas Example VIII demonstrates the use of the inventive process for the hydroformylation of propylene in the presence of tri-alpha-naphthylphosphite. It is to be noted that Examples V and X demonstrate that either carbon monoxide or phosphite adjuvant can be present during the reduction of the rhodium complex. However, it is preferable that the phosphite be present during the hydroformylation process (see experimental procedure in Examples V and X).

Reasonable variations and modifications are possible within the scope of the foregoing disclosure and the appended claims to the invention.

That which is claimed is:

1. A process for the preparation of a catalyst comprising contacting materials consisting essentially of (1) an organorhodium halide of the formula $(L)_n Rh(X)_m$, wherein X is selected from the group consisting of chlorine, bromine, and iodine, L is an unsaturated hydrocarbon group selected from the group consisting of cyclic dienes and cyclic trienes containing from 6 to 16 carbon atoms, $n$ represents an integer of from 1 to 2, $m$ represents an integer of from 1 to 2, and the sum of $n$ plus $m$ is equal to 2 or 3; (2) a compound selected from the group consisting of hydrazine and a hydride of a metal selected from the group consisting of Periodic Table Group IA, IIA, and IIIA metals; and (3) a phosphorus containing adjuvant of the formula $L'_3 P$ wherein each $L'$ is individually selected from the group consisting of aryl and aryloxy radicals having 6 to 12 carbon atoms, alkaryl, aralkyl, alkaryloxy, and aralkoxy radicals having 7 to 12 carbon atoms, and alkyl and alkoxy radicals having 1 to 12 carbon atoms; wherein said contacting is carried out under suitable conditions for forming an intimate mixture of said materials; said intimate mixture being suitable for use as a hydroformylation catalyst.

2. A process in accordance with claim 1 wherein said L is selected from the group consisting of 1,3-cyclohexadienyl, 1,5-cyclooctadienyl, 1,5-cyclooctadiene, 5-sec-butyl-1,3-cyclohexadienyl, dicyclopentadiene, 3,7-dimethyl-1,5-cyclooctadienyl, and cyclododeca-1,5,9-trienyl; wherein each $L'$ is selected from the group consisting of phenyl, naphthyl, p-tolyl, 2,5-dimethylphenyl, 4-tert-butylphenyl, 4-isopentylpheny, benzyl, 4-phenylbutyl, 4-phenylcyclohexyloxy, 2-methylphenoxy, 4-cyclohexylphenoxy, benzyloxy, 2-phenylethoxy, 6-phenylhexyloxy, methyl, ethyl, n-butyl, sec-butyl, tert-octyl, n-dodecyl, methoxy, ethoxy, propyloxy, 4,4-dimethyl cyclohexyloxy, alphanaphthyloxy, and beta-naphthyloxy; and wherein said metal hydride is selected from the group consisting of lithium hydride, sodium hydride, sodium borohydride, cesium hydride, calcium hydride, strontium hydride, barium hydride, and mixtures thereof.

3. A process in accordance with claim 1, wherein said contacting is carried out at a temperature within the range of from about −80°C to about 100°C; the mole ratio of said compound to said organorhodium halide is in the range of about 0.25:1 to about 25:1; and the mole ratio of phosphorus to rhodium is within the range of 100:1 to 1:100.

4. A process in accordance with claim 1 wherein said contacting is carried out at a temperature within the range of from about −80°C to about 100°C; the mole ratio of said compound to said organorhodium halide is in the range of about 1:1 to about 20:1; and the mole ratio of phosphorus to rhodium is within the range of about 2:1 to about 25:1.

5. A process in accordance with claim 1 wherein the contacting is carried out in the presence of an inert diluent.

6. A process in accordance with claim 5 wherein the inert diluent is selected from the group consisting of ethers, aliphatic hydrocarbons, alicyclic hydrocarbons, and aromatic hydrocarbons.

7. A process in accordance with claim 6 wherein said organorhodium halide is $\pi$-cyclododeca-1,5,9-trienylrhodium(III) dichloride, said compound is hydrazine said phosphorus containing adjuvant is tri-alpha-naphthylphosphite, and said inert diluent is anhydrous tetrahydrofuran.

8. A process in accordance with claim 6 wherein said organorhodium halide is $\pi$-cyclododeca-1,5,9-trienylrhodium(III) dichloride, said compound is sodium hydride, said phosphorus containing adjuvant is tri-alpha-naphthylphosphite, and said inert diluent is anhydrous tetrahydrofuran.

9. A process in accordance with claim 6 wherein said organorhodium halide is $\pi$-cyclododeca-1,5,9-trienylrhodium(III) dichloride, said compound is hydrazine, said phosphorus containing adjuvant is tri-phenylphosphite, and said inert diluent is anhydrous tetrahydrofuran.

10. A process in accordance with claim 6 wherein said organorhodium halide is $\pi$-cyclododeca-1,5,9-trienylrhodium(III) dichloride, said compound is sodium borohydride, said phosphorus containing adjuvant is triphenyl phosphite, and said inert diluent is anhydrous tetrahydrofuran.

11. An organorhodium composition consisting essentially of the reaction product obtained by contacting, under suitable conditions to form an intimate mixture, (1) an organorhodium halide of the formula $(L)_n Rh(X)_m$ wherein X is selected from the group consisting of chlorine, bromine, and iodine; L is an unsaturated hydrocarbon group selected from the group consisting of cyclic dienes and cyclic trienes containing from 6 to 16 carbon atoms, $n$ represents an integer of from 1 to 2, $m$ represents an integer of from 1 to 2, and the sum of $n$ plus $m$ is equal to 2 or 3; (2) a compound selected from the group consisting of hydrazine and a hydride of a metal selected from the group consisting of Periodic Table Group IA, IIA, and IIIA metals; and (3) a phosphorus containing adjuvant of the formula $L'_3 P$ wherein $L'$ is individually selected from the group consisting of aryl and aryloxy radicals having 6 to 12 carbon atoms; alkaryl, aralkyl, alkaryloxy, and aralkoxy radicals having 7 to 12 carbon atoms; and alkyl and alkoxy radicals having 1 to 12 carbon atoms; said composition being suitable for use as a hydroformylation catalyst.

12. A composition in accordance with claim 11 wherein said organorhodium halide is $\pi$-cyclododeca-1,5,9-trienylrhodium(III) dichcloride, said compound is hydrazine, said phosphorus containing adjuvant is tri-alpha-naphthylphosphite.

13. A composition in accordance with claim 11 wherein said organorhodium halide is $\pi$-cyclododeca-1,5,9-trienylrhodium(III) dichloride, said compound is sodium hydride, said phosphorus containing adjuvant is tri-alpha-naphthylphosphite.

14. A composition in accordance with claim 11 wherein said organorhodium halide is $\pi$-cyclododeca-1,5,9-trienylrhodium(III) dichloride, said compound is hydrazine, said phosphorus containing adjuvant is triphenylphosphite.

15. A composition in accordance with claim 11 wherein said organorhodium halide is $\pi$-cyclododeca-1,5,9-trienylrhodium(III) dichcloride, said compound is sodium borohydride, said phosphorus containing adjuvant is triphenylphosphite.

16. A composition in accordance with claim 11 wherein said organorhodium halide is $\pi$-cyclododeca-1,5,9-trienylrhodium(III) dichloride.

17. A composition in accordance with claim 11 wherein the mole ratio of said compound to said organorhodium halide is in the range of about 0.25:1 to about 25:1; and the mole ratio of phosphorus to rhodium is within the range of 100:1 to 1:100.

18. A composition in accordance with claim 11 wherein the mole ratio of said compound to said organorhodium halide is in the range of about 2:1 to about 15:1; and the mole ratio of phosphorus to rhodium is within the range of about 2:1 to about 25:1.

19. A process consisting essentially of contacting materials consisting essentially of (1) an organorhodium halide of the formula $(L)_nRh(X)_m$, wherein X is selected from the group consisting of chlorine, bromine, and iodine, L is an unsaturated hydrocarbon group selected from the group consisting of cyclic dienes and cyclic trienes containing from 6 to 16 carbon atoms, $n$ represents an integer of from 1 to 2, $m$ represents an integer of from 1 to 2, and the sum of $n$ plus $m$ is equal to 2 or 3; (2) a compound selected from the group consisting of hydrazine and a hydride of a metal selected from the group consisting of Periodic Table Group IA, IIA, and IIIA metals; and (3) a phosphorus containing adjuvant of the formula $L'_3P$ wherein each $L'$ is individually selected from the group consisting of aryl and aryloxy radicals having 6 to 12 carbon atoms, alkaryl, aralkyl, alkaryloxy, and aralkoxy radicals having 7 to 12 carbon atoms, and alkyl and alkoxy radicals having 1 to 12 carbon atoms; wherein said contacting is carried out under suitable conditions to form an intimate mixture of said materials; said suitable conditions comprising a temperature in the range of about $-80°C$ to about 100°C; the mole ratio of said compound to said organorhodium halide being in the range of about 0.25:1 to about 25:1; the mole ratio of phosphorus to rhodium being in the range of 100:1 to 1:100.

20. A process in accordance with claim 19 wherein said mole ratio of said compound to said organorhodium halide is in the range of about 1:1 to about 20:1 and said mole ratio of phosphorus to rhodium is in the range of about 2:1 to about 25:1.

21. A process in accordance with claim 19 wherein said organorhodium halide is $\pi$-cyclododeca-1,5,9trienylrhodium(III) dichloride.

22. A process in accordance with claim 21 wherein said phosphorus containing adjuvant is tri-phenylphosphite.

23. A process in accordance with claim 22 wherein said compound is hydrazine.

24. A process in accordance with claim 22 wherein said compound is sodium borohydride.

25. A process in accordance with claim 21 wherein said phosphorus containing adjuvant is tri-alpha-naphthylphosphite.

26. A process in accordance with claim 25 wherein said compound is sodium hydride.

27. A process in accordance with claim 25 wherein said compound is hydrazine.

28. An organorhodium composition consisting essentially of the reaction product of claim 19.

29. An organorhodum composition consisting essentially of the reaction product of claim 23.

30. An organorhodium composition consisting essentially of the reaction product of claim 24.

31. An organorhodium composition consisting essentially of the reaction product of claim 26.

32. An organorhodium composition consisting essentially of the reaction product of claim 27.

* * * * *